(12) United States Patent
Richey, II et al.

(10) Patent No.: US 8,800,556 B2
(45) Date of Patent: Aug. 12, 2014

(54) ELECTRONIC OXYGEN CONSERVER AND FILLING UNIT

(75) Inventors: Joseph B. Richey, II, Chagrin Falls, OH (US); Thomas Strothmann, Bramsche (DE)

(73) Assignee: Invacare Corporation, Elyria, OH (US)

( * ) Notice: Subject to any disclaimer, the term of this patent is extended or adjusted under 35 U.S.C. 154(b) by 2180 days.

(21) Appl. No.: 11/451,096

(22) Filed: Jun. 12, 2006

(65) Prior Publication Data
US 2008/0000476 A1 Jan. 3, 2008

(51) Int. Cl.
*F16K 31/02* (2006.01)

(52) U.S. Cl.
USPC .................. 128/204.21; 128/204.18; 141/18; 141/2; 141/94

(58) Field of Classification Search
USPC ......... 128/204.21, 205.22, 204.18; 141/18, 2, 141/94
See application file for complete search history.

(56) References Cited

U.S. PATENT DOCUMENTS

| | | | |
|---|---|---|---|
| 4,584,996 A | 4/1986 | Blum | |
| 5,529,465 A | 6/1996 | Zengerle et al. | |
| 5,755,408 A | 5/1998 | Schmidt et al. | |
| 6,105,904 A | 8/2000 | Lisy et al. | |
| 6,152,134 A | 11/2000 | Webber et al. | |
| 6,220,244 B1 | 4/2001 | McLaughlin | |
| 6,354,839 B1 | 3/2002 | Schmidt et al. | |
| 6,364,161 B1 | 4/2002 | Pryor | |
| 6,427,690 B1 | 8/2002 | McCombs et al. | |
| 6,484,721 B1 | 11/2002 | Bliss | |
| 6,612,307 B2 | 9/2003 | Byrd | |
| 6,651,658 B1 | 11/2003 | Hill et al. | |
| 6,662,081 B1 * | 12/2003 | Jacober et al. | 700/242 |
| 6,743,021 B2 | 6/2004 | Prince et al. | |
| 6,752,152 B2 | 6/2004 | Gale et al. | |
| 7,013,726 B1 | 3/2006 | Drummond et al. | |
| 7,264,026 B2 * | 9/2007 | Gruber et al. | 141/113 |
| 2002/0096174 A1 * | 7/2002 | Hill et al. | 128/205.11 |
| 2003/0140924 A1 * | 7/2003 | Aylsworth et al. | 128/204.26 |
| 2004/0055600 A1 * | 3/2004 | Izuchukwu | 128/205.15 |
| 2005/0092321 A1 * | 5/2005 | Aylsworth et al. | 128/200.24 |
| 2006/0124128 A1 * | 6/2006 | Deane et al. | 128/204.21 |
| 2006/0157058 A1 * | 7/2006 | Aylsworth et al. | 128/204.23 |
| 2006/0174882 A1 * | 8/2006 | Jagger et al. | 128/201.25 |
| 2006/0219245 A1 * | 10/2006 | Holder | 128/204.26 |

OTHER PUBLICATIONS iACTIV Corporation, GP-03X MEMS MicroValve, version 1.2, Feb. 2003, 1 pg.

(Continued)

*Primary Examiner* — Justine Yu
*Assistant Examiner* — Colin W Stuart
(74) *Attorney, Agent, or Firm* — Calfee, Halter & Griswold LLP

(57) ABSTRACT

A respiratory system and method includes a filling unit for filling a portable bottle of respiratory gas and a conserver for mounting on such a bottle. A battery on the conserver may be recharged when the bottle is placed on the filing unit. The conserver may include electric timing circuitry operative to control the timing of pulsed flow of respiratory gas from the conserver, and an external electrical coupler to enable adjustment of the timing of the pulsed flow. The conserver may include at least one sensor operative to sense the reversal of flow between exhalation and inhalation, the conserver being operative to commence a respiratory gas delivery pulse in response to the sensing of the reversal of flow.

9 Claims, 2 Drawing Sheets

(56) References Cited

OTHER PUBLICATIONS

Invacare Owner's Operator and Maintenance Manual, Venture, Demand Oxygen Delivery Deivce and System, part No. 1093845, 28 pgs.

Web page from http://www.grogans.com, Grogan's Healthcare Supply, Chad Therapeutics System Mini 02 Portable Oxylite Chad Therapeutics, CHADPS-150, 1 pg.

Web page from http://etrode.com, 02 EasyPulse 5 Oxygen Conserving Regulator, product # WE198705, 2 pgs.

Web pages from http://pulmolab.com, Total 02 Delivery System, 400 Series Conserver, Cypress OxyPneumatic Conserver and Sequoia Conserver, 9 pgs.

Web pages from http://store.noahsarkhomecare.com, Chad Therapeutic OxyMatic Conserver, Model 401A, 3 pgs.

Web pages from http://www.chadtherapeutics.com, Lotus Electronic Oxygen Conserver, 5 pgs.

* cited by examiner

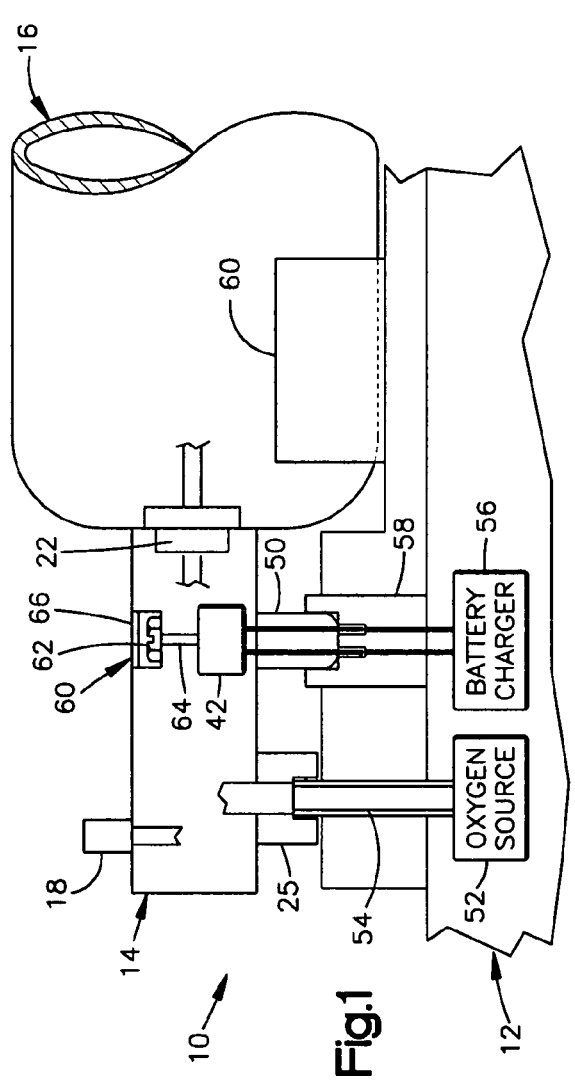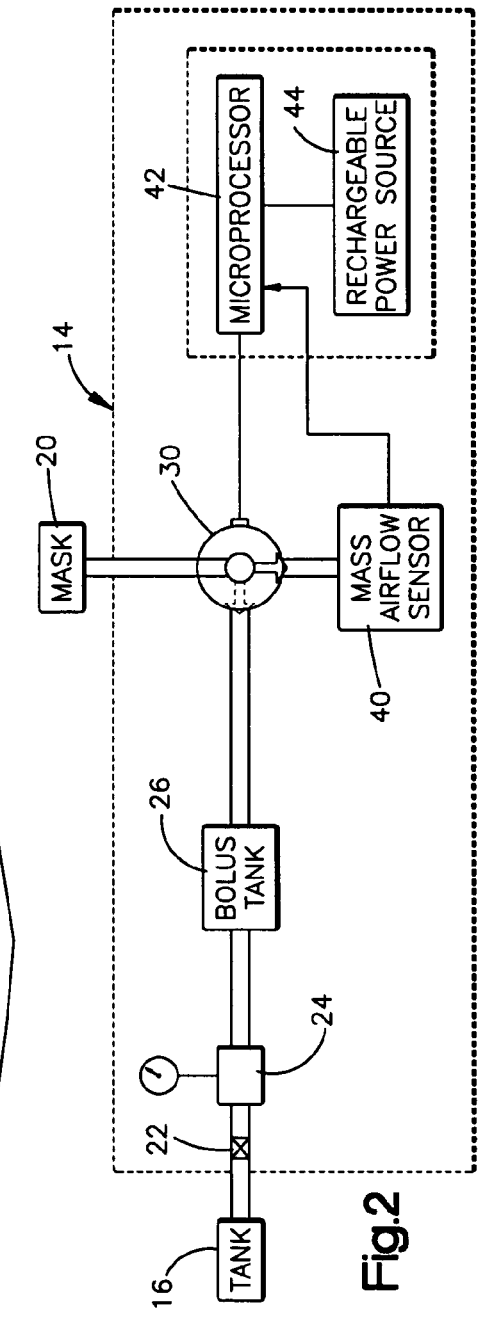

ELECTRONIC OXYGEN CONSERVER AND FILLING UNIT

BACKGROUND OF THE INVENTION

This application relates to a respiratory system and method. In one embodiment, this application relates to a filling unit for filling a portable bottle of respiratory gas when the bottle is engaged with the filling unit, and to a battery-powered conserver for mounting on such a bottle.

BRIEF DESCRIPTION OF THE DRAWINGS

In the accompanying drawings:

FIG. 1 is a schematic representation of a portion of a filling unit shown connected with a conserver;

FIG. 2 is a schematic diagram of a conserver; and

DETAILED DESCRIPTION

Figure 3:
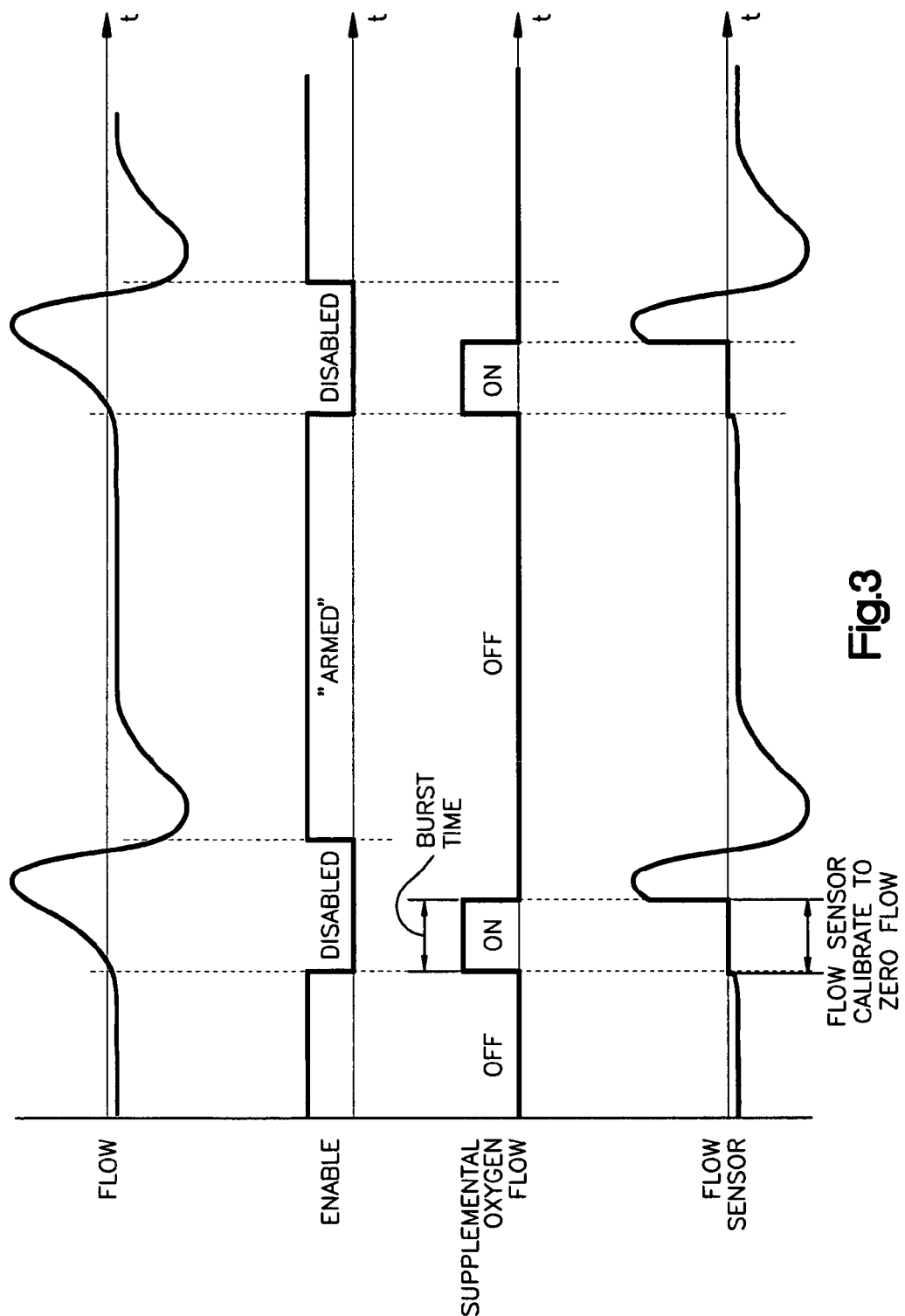
FIG. 3 is a graph showing aspects of the operation of the conserver.

This application relates to a respiratory system and method. In one embodiment, this application relates to a filling unit for filling a portable bottle of respiratory gas when the bottle is engaged with the filling unit, and to a battery-powered conserver for mounting on such a bottle, and to related methods. The invention is applicable to systems and methods of various different constructions and modes of operation. As representative of the invention, FIG. 1 illustrates schematically a respiratory system 10.

The system 10 includes a filling unit 12 and a conserver 14. The conserver 14 is shown mounted on a bottle 16. The bottle 16 may be any type or size or configuration of portable bottle of respiratory gas. Typically such bottles are filled with oxygen-enriched gas having an oxygen concentration of 90% to 95% or more. The gas is stored under pressure in the bottle 16, at a pressure of up to 2,000 psi or more. The gas is dispensed from the bottle 16 through the conserver 14.

The conserver 14 is removably mounted on the bottle 16, and thus items that are on the conserver, or are part of the conserver, are on the bottle. The conserver 14 includes a port 18 for connection of a mask 20, such as a nasal mask, through which the gas is dispensed to a wearer of the mask. The conserver 14 is operative generally to dispense measured pulses or bursts or puffs of gas to the wearer, rather than a continuous stream of gas, thus conserving the gas in the bottle 16.

The conserver 14 includes a gas inlet port 22 for receiving gas from the bottle 16. The gas inlet port 22 connects with a regulator 24, in the conserver 14, that can limit the pressure and/or other flow characteristics of the gas that flows from the bottle 16 into the conserver. Gas that is received into the conserver 14 is directed to the mask 20 via the mask port 18.

The conserver 14 includes a fill tube 25 for receiving respiratory gas for refilling the bottle 16. The conserver 14 also includes a bolus tank 26. The bolus tank 26 holds a small amount of gas, typically less than or equal to the amount needed for one breath (one pulse of gas to the mask). The output of the bottle 16 flows through the regulator 24 into the bolus tank 26.

The output of the bolus tank 26 is directed to a control valve 30 in the conserver. The control valve 30 is preferably a three-way valve. The valve 30 is electrically operative to connect the mask 20 with either (a) the output of the bolus tank 26, or (b) a sensor shown schematically at 40.

The sensor 40 is preferably but not necessarily a mass flow sensor. The sensor 40 is fluidically connected with the mask 20, by means of the valve 30, in such a way that inhalation or exhalation by the user of the mask is sensed by the sensor. The valve 30 is electrically powered to move between a first position in which the mask 20 is connected fluidically with the bolus tank 26, and a second position in which the mask is connected fluidically with the sensor 40. The valve 30 may be a latching valve that stays in whichever position it is put into, until a subsequent pulse of electricity is delivered. A momentary pulse of power only is needed to change the position of the valve 30.

The position of the valve 30 is controlled by a signal from a microprocessor 42 that is included as part of the conserver 14. The microprocessor 42 is any type of electric or electronic circuitry operative to control the various functions of the conserver 14 and may include one or more algorithms for determining pulse characteristics based on the output of the sensor 40. The sensor 40 is electrically connected with the microprocessor 42 to make the output of the sensor usable by the microprocessor. The microprocessor 42 is powered by a rechargeable power source 44 in the conserver 14. The power source 44 is preferably a rechargeable battery. The power source 44 also powers the valve 30 and the sensor 40 (if the sensor needs power).

The conserver 14 includes a coupler shown schematically at 50. The coupler 50 is operative to connect the rechargeable battery 44 with an external (to the conserver) source of electrical power for recharging the battery. The coupler 50 may be, for example, one or more metal contacts that are electrically connected with the battery 44. The coupler 50 may also be a portion of an inductive coupling apparatus by which power can be transferred into the battery to recharge the battery 44.

The filling unit 12 includes an oxygen source 52 that is typically (but need not be) a concentrator. The oxygen source 52 is connected with a fill nozzle 54 on the filling unit 12 for delivering oxygen to a portable bottle 16 to be filled, in a manner as described below.

The filling unit 12 includes a power source. The power source may be, for example, a battery charger 56. The battery charger 56 is connected with a coupler 58. The coupler 58 may be, for example, one or more metal contacts that are electrically connected with the battery charger 56. The coupler 58 may also be a portion of an inductive coupling apparatus by which the battery 44 can be recharged, in a manner as described below.

The filling unit 12 is optionally provided with a cradle 60. The cradle 60 is a device or structure, or a portion of the filling unit 12, that supports a portable bottle 16 of respiratory gas on the filling unit, during the process of refilling the bottle, in such a manner that the conserver battery 44 can simultaneously be recharged.

When the bottle 16 needs to be refilled, it is placed on or otherwise associated with the filing unit 12. For example, the bottle 16 may be placed on the cradle 60. The fill tube 25 on the conserver 14 is manually aligned with and connected with the fill nozzle 54 on the filling unit 12. The cradle 60 on the filling unit 12 helps to align and support the bottle 16 on the filling unit. The bottle 16 is thereby connected in fluid communication with the filling unit 12. Oxygen from the filling unit 12 is delivered to the bottle 16, through the conserver 14.

During the alignment and positioning of the bottle 16 on the filling unit 12, the coupler 50 on the conserver 14 engages or is otherwise electrically associated with the coupler 58 of the filling unit. As a result, electrical power flows from the battery charger 56 of the filling unit 12, to the rechargeable battery 44 of the conserver 14. The battery 44 of the conserver 14 is thereby recharged. This recharging of the battery 44 occurs simultaneously with the refilling of the bottle 16.

The filling of the bottle 16, and the charging of the battery 44, may be operationally connected. For example, the filling unit 12 may be set up so that oxygen cannot flow from the filling unit unless the conserver battery 44 is electrically connected with the charger 56. This interaction can help to prevent a bottle 16 from being refilled without its conserver battery 44 also being recharged. This can prevent a filled bottle 16 from being taken from the filling unit, with a non-charged battery 44.

In addition, the battery 44 of the conserver 14 is preferably designed to function for a period of time substantially longer than the time needed to discharge the bottle 16. This can help to ensure that the conserver 14 does not cease to function when in use on a bottle 16 with some remaining oxygen.

The mass flow sensor 40 is operative to sense both inhalation and exhalation by the wearer of the mask, and is thereby useful in timing the delivery of the oxygen pulses. As a result, the conserver can provide for improved timing of the oxygen pulses, as well as improved calibration of the mass flow sensor 40.

Specifically, as shown schematically in FIG. 3, the first or upper line in FIG. 3 graphs the flow of gas between the mask and the wearer. This flow rate is dependent on the availability of oxygen as provided from the conserver 14, and the inhalation or exhalation characteristic of the wearer. A positive reading (above the line) denotes inhalation, and a reading below the line denotes exhalation.

The second line in FIG. 3 represents the status of the electrical connection between the output of the mass flow sensor 40 and the microprocessor 42. Specifically, the circuitry in the microprocessor 42 is operative either to address or to "ignore" the reading from the sensor 40. In the "disabled" portion of the line, the reading from the sensor 40 is not taken into account by the microprocessor 42, in determining whether to trigger the valve 30 to direct gas to the mask 20. The valve 30 is not "armed" until the mass flow sensor 40 indicates that the flow is definitely in an exhalation portion of the curve. Electrically disconnecting the output of the sensor 40 from the ECU 42, in this manner, can help to eliminate false triggering of the gas flow.

The third line in FIG. 3 graphs the on/off condition of the supplemental oxygen flow provided by the conserver 14 to the mask 20. This is controlled by the position of the valve 30. When the line is down, the valve 30 blocks flow between the bolus tank 26 and the mask 20, and supplemental oxygen is not provided. When the line is up, the valve 30 opens the fluid connection between the bolus tank 26 and the mask 20, and supplemental oxygen is provided to the user through the control valve and the mask.

The fourth line in FIG. 3 graphs the output of the flow sensor 40, which is indicative of inhalation and exhalation. A reading above the line indicates inhalation and a reading below the line indicates exhalation. During the burst time (valve open time) for the supplemental oxygen flow, the sensor 40 is not connected fluidically with the mask 20. In this time period, the sensor 40 can be calibrated to zero flow (no inhalation, no exhalation). The rising of the line represents inhalation by the wearer, and the subsequent falling of the line indicates exhalation by the wearer. Being able to calibrate the zero air flow level, means that the transitions between exhalation and inhalation can be detected in a very accurate fashion.

It can be seen that the supplemental oxygen is provided just prior to the inhalation by the wearer of the mask 20. This puts the oxygen in the mask 20, available for use by the wearer, prior to inhalation and during the beginning of the inhalation period (which is when most gas is taken up by the wearer).

Provision of the supplemental oxygen at this time is made possible by the fact that the sensor is operative to sense the absolute flow of gas into and out of the mask. Specifically, the sensor is operative to sense the reversal of flow between exhalation and inhalation. This sensing provides, or enables, earlier and therefore better triggering for the inhalation puff. In addition, this sensing prevents re-triggering (unintended flow after the sensor shut-off period shown in the fourth line ends).

In accordance with another aspect of the invention, the conserver 14 includes an on-board adjustment mechanism to enable adjustment of the duration of the pulsed flow of oxygen. Some patients might require longer pulses of oxygen, and other patients might require shorter pulses of oxygen. Typical known conservers have the pulse duration set at the factory and are not adjustable by the user or by a clinician.

The adjustment mechanism of the conserver 14 includes an adjustment port shown schematically at 61. The port 61 includes an adjustment mechanism 62 for adjusting the pulse duration. The adjustment mechanism 62 is electrically connected with the microprocessor by one or more lead wires indicated schematically at 64. The adjustment mechanism 62 might be, for example, a knob or screw or other type of control that is manually adjustable to set pulse duration. The adjustment mechanism 62 might, alternatively, include electrical contacts, such as a socket or plug, for engagement with an external device. The external device might be a hand-held computer for reprogramming the microprocessor 42 of the conserver 14. The port 61 may optionally include a door or other type of closure 66, in order to block access to the adjustment mechanism 62 by unauthorized persons.

Having described the invention, we claim:

1. An electronic conserver for use on a bottle of respiratory gas that is refillable when engaged with a filling unit, the conserver comprising:
    a rechargeable battery;
    fluid connections for placing the conserver in fluid communication with the filling unit
    and for placing the conserver in fluid communication with the bottle;
    a coupler for electrically coupling the battery with a battery charger of a filling unit when the bottle is engaged with the filling unit by the fluid connections;
    wherein respiratory gas is prevented from flowing from the filling unit to the bottle unless the rechargeable battery is electrically connected to the battery charger by the coupler.

2. A conserver as set forth in claim 1 wherein the conserver is connectable to a patient interface, wherein the conserver further comprises a sensor operative to sense absolute gas flow through the patient interface.

3. A conserver as set forth in claim 2 wherein the sensor is operative to analyze positive and negative gas flows relative to a baseline gas flow for a reversal of gas flow between exhalation and inhalation.

4. A conserver as set forth in claim 2 wherein the sensor is a mass flow sensor that is offline during a portion of a respiratory cycle to enable baseline calibration of the sensor.

5. A conserver as set forth in claim 1 further comprising a patient interface port for connection with a patient interface, the conserver comprising a sensor operative to analyze positive and negative gas flows relative to a baseline gas flow for a reversal of gas flow between exhalation and inhalation and a valve selectively operable to place the patient interface port in fluid communication either with the sensor or with a gas inlet port.

6. A conserver as set forth in claim 5 wherein the valve is a latching valve.

7. A conserver as set forth in claim 1 comprising electric timing circuitry operative to control timing of pulsed flow of respiratory gas from the conserver, and an external electrical coupler that is electrically connected with the timing circuitry to enable adjustment of the timing of the pulsed flow of respiratory gas.

8. A conserver as set forth in claim 7 wherein the external electrical coupler is operative to receive an electrical control signal from an external electrical source to adjust the timing of pulsed flow of respiratory gas from the conserver.

9. A conserver as set forth in claim 7 wherein the external electrical coupler includes a manual adjustment for adjusting the timing of the pulsed flow of respiratory gas.

\* \* \* \* \*